United States Patent [19]

Stormont et al.

[11] Patent Number: 4,737,712
[45] Date of Patent: Apr. 12, 1988

[54] ISOLATED POWER TRANSFER AND PATIENT MONITORING SYSTEM WITH INTERFERENCE REJECTION USEFUL WITH NMR APPARATUS

[75] Inventors: Robert S. Stormont; Randall H. Buchwald, both of Waukesha, Wis.; Ralph S. Hashoian, Natick, Mass.

[73] Assignee: General Electric Company, Milwaukee, Wis.

[21] Appl. No.: 948,201

[22] Filed: Dec. 31, 1986

[51] Int. Cl.⁴ ............................................. G01R 33/20
[52] U.S. Cl. ................................... 324/307; 324/322; 324/96
[58] Field of Search .............. 324/300, 307, 318, 319, 324/320, 322, 96, 313, 72; 128/653

[56] References Cited

U.S. PATENT DOCUMENTS 4,011,745  3/1977  Gatos et al. .............................. 73/23
4,628,264  12/1986  Rzedzian .............................. 324/322

*Primary Examiner*—Michael J. Tokar
*Attorney, Agent, or Firm*—Mark L. Mollon; Douglas E. Stoner

[57] ABSTRACT

There is provided a power source for continuously energizing electrically isolated devices used to monitor the physiological state of a subject undergoing an examination in an NMR scanner having a magnet, RF and gradient coils. The power source is made up of a first element for generating energy of one type and a second element for receiving this energy and converting it to a second energy type used to energize the electrically isolated devices. The first and second elements are operatively coupled to one another through an electrically isolated medium to permit continuous transfer of energy from the first to the second element and to reject interference due to the NMR apparatus subsystems. In one embodiment the first element may be an array of light-emitting diodes, while the second element may be an array of photovoltaic cells. In another embodiment, the first and second elements may be ultrasonic transducers coupled through air or a ceramic substrate.

5 Claims, 2 Drawing Sheets

ISOLATED POWER TRANSFER AND PATIENT MONITORING SYSTEM WITH INTERFERENCE REJECTION USEFUL WITH NMR APPARATUS

BACKGROUND OF THE INVENTION

This invention relates in general to patient-connected electrical equipment. More specifically, this invention relates to providing an isolated power source which will function in the presence of strong magnetic and radio frequency (RF) fields, for example, such as those associated with nuclear magnetic resonance (NMR) apparatus to monitor physiological function, such as heart rate, of a living human or animal subject undergoing examination.

NMR has been developed as an imaging modality utilized to obtain images of anatomical features of human patients, for example. Such images depicting nuclear spin distribution (typically, protons associated with water and tissue), spin-lattice relaxation time $T_1$, and/or spin-spin relaxation time $T_2$ are of medical diagnostic value in determining the state of health of the tissue examined. Imaging data for constructing NMR images can be collected using one of many available techniques, such as multiple-angle projection reconstruction and Fourier transform (FT). Typically, such techniques comprise scanning the patient with a pulse sequence made up of a plurality of sequentially implemented views. Each view may include one or more NMR experiments, each of which comprises at least a radio-frequency pulse and a magnetic field gradient pulse to encode spatial information into the NMR signal.

In some situations, it is desirable to physiologically monitor the subject during an NMR scan. This may be necessitated for medical reasons, in the case of an infirm patient, or to acquire signals in response to a change in a physiological characteristic of the subject and to use the signal to control some aspect of the scanning process, such as cardiac gating or respiratory compensation.

Typically, physiological signals are acquired in a well-known manner using electrodes attached to the body of the subject. The electrodes are connected by leads and additional cable, as necessary, to suitable electrical apparatus, for example, an electrocardiogram (ECG) amplifier which may be part of a patient monitor system. NMR imaging systems, however, create a difficult environment for patient monitoring systems to operate. For example, strong, steady-state magnetic fields, RF transmit pulses and audio frequency gradient field pulses compound the problems of monitoring low level physiological signals while maintaining a high degree of isolation and interference rejection between the patient and earth ground.

The conventional approach to isolated patient monitoring systems consists, typically, of providing an isolated small signal amplifier system (i.e., the ECG amplifier) for direct connection to the physiologic transducers (i.e., ECG leads). The output of this amplifier system is then transmitted to the grounded (non-isolated) instrumentation by means of, for example, a telemetry system which maintains the patient isolation. The isolated system, however, still requires a power source; either batteries or an isolated power supply. Batteries are not preferred since they require periodic replacement and occasionally deplete prematurely. Power supplies designed for conventional patient monitoring applications are typically dc-dc converters employing ferrite transformers with isolated windings. While these devices provide ample, regulated dc voltages and maintain high 60 Hz isolation, the ferrite transformer components saturate in high magnetic fields (e.g., 1.5 T) thereby rendering them unusuable in an NMR environment.

Applicants herein have discovered and claimed as their invention a means for applying power continuously to an isolated patient monitoring system, while maintaining a high degree of electrical isolation and interference rejection.

SUMMARY OF THE INVENTION

In accordance with the invention, there is provided a power source for continuously energizing electrically isolated devices used to monitor the physiological state of a subject undergoing an examination in an NMR scanner having a magnet, RF and gradient coils. The power source is made up of a first element for generating energy of one type and a second element for receiving this energy and converting it to a second energy type used to energize the electrically isolated devices. The first and second elements are operatively coupled to one another through an electrically isolated medium to permit continuous transfer of energy from the first to the second element and to reject interference due to the NMR apparatus subsystems.

In one embodiment the first element may be an array of light-emitting diodes, while the second element may be an array of photovoltaic cells. In another embodiment, the first and second elements may be ultrasonic transducers coupled through air or a ceramic substrate.

BRIEF DESCRIPTION OF THE DRAWINGS

The features of the invention believed to be novel are set forth with particularity in the appended claims. The invention itself, however, both as to its organization and method of operation, together with further objects and advantages thereof, may best be understood by reference to the following description taken in conjunction with the accompanying drawings in which:

DETAILED DESCRIPTION OF THE INVENTION

Figure 1:
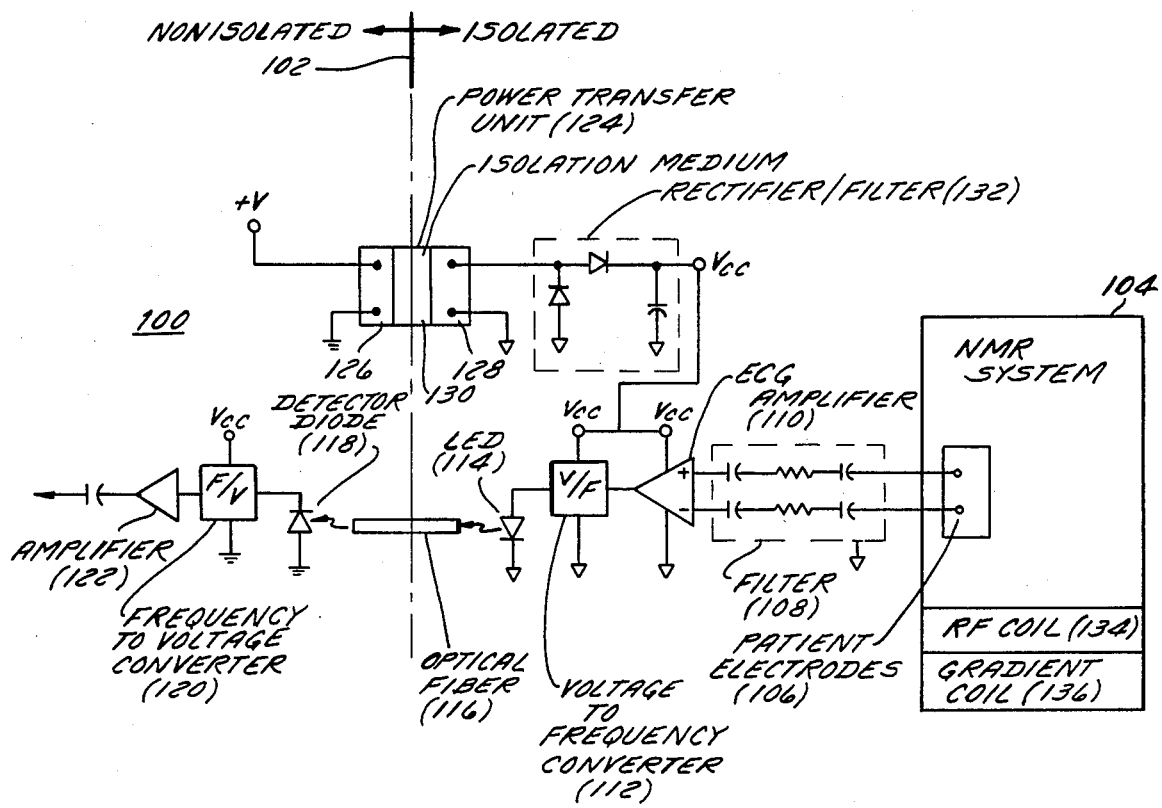
FIG. 1 depicts in block schematic form an isolated patient monitoring system including means for transferring power to the isolated components of the system in accordance with the invention.

FIG. 1 depicts in schematic form a system for transferring power to the isolated portion of a patient monitoring system, generally designated 100, in accordance with the invention. In general, the isolated portions of the system, as shown in FIG. 1, lie to the right of the line identified by reference numeral 102. Of course, parts of an NMR system 104, such as the various subsystem power supplies need not be isolated because they are not electrically connected to the patient. The patient monitoring system includes patient electrodes 106 which in use are connected to a patient (not shown). For example, ECG signals detected by the electrodes are applied through a filter 108 to a signal conditioning amplifier, such as an ECG amplifier 110. The output of the ECG amplifier is applied to a voltage-to-frequency converter 112 which converts the amplitude variations in the analog ECG waveform to an analog signal having corresponding frequency variations. The signal with the frequency variations is applied to an LED 114, the optical output of which is applied to the input end of an optical fiber link 116. At the other end of the optical fiber link a detector diode 118 converts the optical signal back to an electrical signal. The optical fiber link provides optical isolation between the patient and the remaining patient monitoring circuitry to the left of line 102. The signal detected by diode 118 is applied to a frequency-to-voltage converter 120 and through a conditioning amplifier 122 to circuitry (not shown) for utilizing the ECG signal such as, for example, gating or monitor display apparatus.

The ECG amplifier 110 and voltage-to-frequency converter 112 are the elements in the isolated portion of the patient monitoring system requiring continuous supply of power in order to function properly. In accordance with the invention, this is accomplished by means of a power-transfer unit 124 which will be more fully discussed hereinafter. In general, the power transfer unit is made up of a transducer element 126 energized by a source of voltage V on the non-isolated side of the system. Element 126 is coupled to a second transducer element 128 for receiving power therefrom through an electrically isolated medium 130. The output of element 128 is applied to a rectifier/filter circuit 132. The output voltage $V_{cc}$ of the rectifier/filter circuit is used to continuously energize ECG amplifier 110 and voltage frequency converter 112. The isolation medium 130 acts to not only isolate the patient electrodes from earth ground, but also to reject interference created by RF coil 132 and gradient coil 136 which form part of the NMR system 104.

Figure 2:
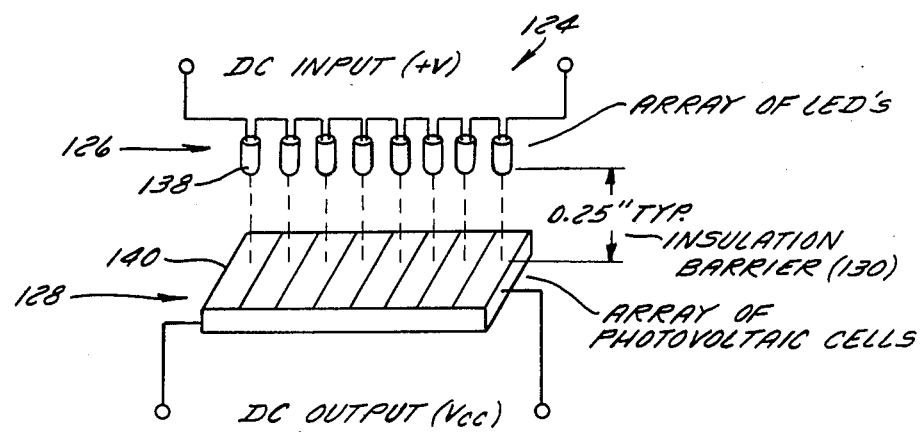
FIG. 2 depicts one embodiment of a power transfer unit in accordance with the invention which is made up of an array of light-emitting diodes (LED) which illuminate an array of photovoltaic cells.

Referring now to FIG. 2, there is shown one specific embodiment of a power transfer unit 124 in which element 126 at the input end of the device is comprised of an array of series-connected LED's generally designated by reference numeral 138. When the LED's are energized by a dc voltage, the optical output of the light-emitting diodes traverses isolation barrier 130 and impinges on an array of photovoltaic cells 140, whereupon it is converted to a dc output voltage $V_{cc}$ used to energize the isolated components of the patient monitoring system. The isolation barrier in this embodiment typically comprises air and the separation between the LED's and the photovoltaic cells is selected to have at least a 3,000 volts breakdown characteristic. It has been found, for example, that a separation of approximately ¼ inch is sufficient for this purpose. In this and subsequently described embodiments the larger the separation between the input and output elements, the lower the capacitive coupling, providing better isolation and interference rejection. The LED devices may be of any convenient type of the high output type which are spectrally compatible with the photovoltaic cell type. In the preferred embodiment, the LED's are of the type generally known as gallium-aluminum-arsenide devices. The photovoltaic cells are of conventional design and are of the type known as silicon photocells.

In a typical application it has been found that eight series-connected photovoltaic cells are sufficient to provide an output of approximately 3.2 volts at approximately 5 mA. Such relatively low output voltage and current necessitates that the circuits powered thereby, such as the ECG amplifier and voltage-to-frequency converter be of the low power consumption type. Such low power consumption circuits may be conveniently of the linear CMOS-type semiconductor devices. It will be, of course, recognized that the type of LED, photovoltaic cell device employed, as well as other parameters, such as the dimension of the isolation barrier and the number of individual devices employed may be varied and such changes are considered to be within the scope of the present invention.

Figure 3:
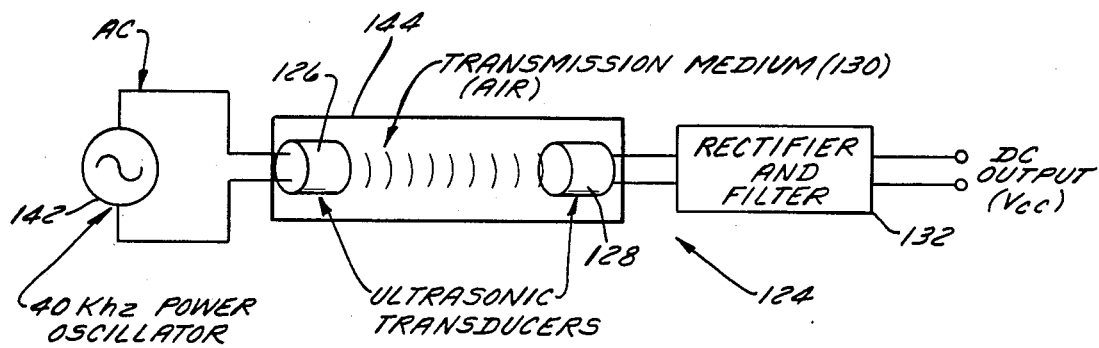
FIG. 3 depicts another embodiment of a power transfer unit which consists of a pair of ultrasonic transducers for continuously transmitting power across the transmission medium.

Reference is now made to FIG. 3 which depicts another preferred embodiment of an inventive power transfer unit 124. In this embodiment, elements 126 and 128 comprise ultrasonic transducer elements coupled across electrically isolating transmission medium 130, such as air. Elements 126 and 128 are of the conventional type having ability to convert electrical energy into mechanical energy and vice versa. Thus, element 126 is coupled to a power oscillator 142 having a frequency of, for example, 40 kHz. The electrical energy of the oscillator is converted into mechanical energy and is transmitted across the isolating medium to element 128 where the mechanical energy is converted back into electrical energy. This electrical energy, after filtering and rectification by a rectifier and filter 132, is applied to the isolated devices to be energized.

The spacing between elements 126 and 128 determines the degree of coupling and therefore the efficiency of the power transfer. The assembly of the two transducers into a single structure may therefore require some means for positional adjustment, such as by varying the distance therebetween within transducer mounting frame 144.

Figure 4A:
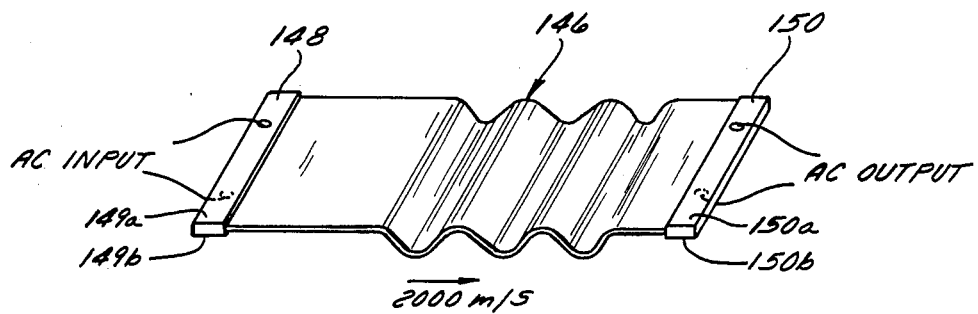
FIGS. 4A and 4B depict yet another embodiment of a power transfer unit employing an ultrasonic transducer of the type known as a thin film piezoelectric ceramic coupler.
Figure 4B:
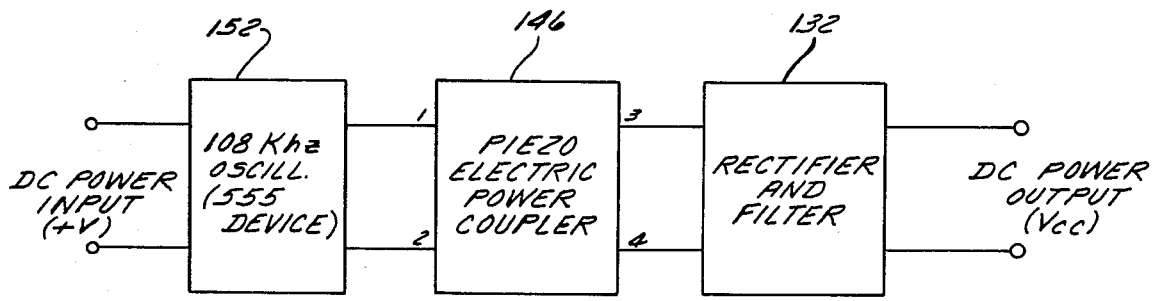

FIG. 4A depicts a prederred embodiment of the acoustical method for coupling power continuously to isolated load devices. This method employs an integrally coupled piezoelectric device of the type referred to as thin-film piezoelectric ceramic coupler. The conventional application of such devices is in the field of high energy power coupling where such devices are used to generate short switching pulses for such devices as triacs. Such devices are constructed on a single ceramic substrate, such as that designated 146, and wherein an input piezoelectric element, such as that designated 148, is located at one end of the ceramic substrate, while the output element, such as that designated 150, is located at the other. Each of the elements 148 and 150 are made up of electrical contact points affixed to the ends of the ceramic substrate 146. By way of example, element 148 is made up of electrically conductive areas 149a and 149b attached to opposite surfaces of the ceramic substrate. Leads are attached to areas 149a and 149b for applying input power. Element 150 is similarly constructed with conductive areas 150a and 150b attached to the output end of the substrate. Such devices are disclosed and claimed in U.S. Pat. No. 4,584,499 and U.S. patent application Ser. No. 551,452, both of which are incorporated herein by reference. An alternating signal is applied to the input device at terminals 1 and 2 from an oscillator, such as that designated with reference numeral 152 in FIG. 4B. The alternating current in the power source is converted from electrical to mechanical energy in the input element and the vibrations from this device are coupled across the substrate to the second device which reconverts the acoustic wave to electrical energy at the output terminals 3 and 4 in FIG. 4B. Electrical isolation between the input and output of these devices is provided by the electric-mechanical-electric energy conversion. Such devices have the ability to withstand up to 4,000 v. dc. Maximum coupling efficiency for this device occurs at its resonant frequency so that the oscillator or power source 152 in FIG. 4B must operate at that frequency. As is seen in FIG. 4B for one device oscillations at 108 kHz have been found satisfactory.

While this invention has been described with reference to particular embodiments and examples, other modifications and variations will occur to those skilled in the art in view of the above teachings. Accordingly, it should be understood that within the scope of the appended claims the invention may be practiced otherwise than is specifically described.

The invention claimed is:

1. In an NMR apparatus having a magnet for generating a magnetic field, RF coils for generating RF transmit pulses, gradient coils for generating gradient magnetic field pulses, and a power source for providing electrically isolated power to devices used to monitor the physiological state of a scan subject, the improvement wherein said power source comprises:

a first element for generating power of one type;

a second element for receiving power from said first element and converting the received energy to a different energy type used to continuously provide power to electrically isolated devices used to monitor the physiological state of a scan subject;

said first and second elements being operatively coupled to one another through an electrically isolating medium so as to permit continuous transfer of power of said one type from said first element to said second element and to reject interference due to the magnetic field, and RF transmit and gradient magnetic field pulses, said electrically isolating medium being immune to the effects of the NMR system magnetic field.

2. The apparatus of claim 1 wherein said first element comprises an array of light-emitting diodes and said second element comprises an array of photovoltaic cells operatively coupled to said first element.

3. The apparatus of claim 1 wherein said first and second elements comprise ultrasonic transducer elements operatively coupled to one another.

4. The apparatus of claim 1 wherein said first and second elements comprise piezoelectric elements coupled to one another through a ceramic substrate.

5. The apparatus of claim 1 wherein the degree of coupling between said first and second elements is adjustable.

* * * * *